United States Patent
Franzen et al.

(10) Patent No.: US 9,245,727 B2
(45) Date of Patent: Jan. 26, 2016

(54) VOLTAGE SUPPLIES FOR MASS SPECTROMETERS

(71) Applicant: Bruker Daltonik GmbH, Bremen (DE)

(72) Inventors: Jochen Franzen, Bremen (DE); Claus Köster, Lilienthal (DE)

( * ) Notice: Subject to any disclaimer, the term of this patent is extended or adjusted under 35 U.S.C. 154(b) by 0 days.

(21) Appl. No.: 13/886,641

(22) Filed: May 3, 2013

(65) Prior Publication Data

US 2014/0117220 A1    May 1, 2014

(30) Foreign Application Priority Data

May 3, 2012  (DE) .......... 10 2012 008 972

(51) Int. Cl.
*H01J 49/26* (2006.01)
*H01J 49/42* (2006.01)

(52) U.S. Cl.
CPC .............. *H01J 49/26* (2013.01); *H01J 49/425* (2013.01)

(58) Field of Classification Search
USPC ................................. 250/282, 288, 281, 209
See application file for complete search history.

(56) References Cited

U.S. PATENT DOCUMENTS

| | | | |
|---|---|---|---|
| 4,311,669 A | 1/1982 | Spangler | |
| 5,155,357 A * | 10/1992 | Hemond | H01J 49/328 250/281 |
| 5,313,061 A * | 5/1994 | Drew | B01D 59/44 250/281 |
| 5,719,392 A | 2/1998 | Franzen | |
| 5,869,832 A * | 2/1999 | Wang et al. | 250/288 |
| 6,459,079 B1 * | 10/2002 | Machlinski et al. | 250/286 |
| 7,173,240 B2 * | 2/2007 | Seaward et al. | 250/288 |
| 8,547,104 B2 * | 10/2013 | Barrett | 324/388 |
| 2005/0051720 A1 * | 3/2005 | Knecht et al. | 250/288 |
| 2012/0112056 A1 * | 5/2012 | Brucker et al. | 250/282 |

FOREIGN PATENT DOCUMENTS

| | | |
|---|---|---|
| DE | 916677 B1 | 8/1954 |
| DE | 19650419 C1 | 6/1998 |
| DE | 102007024858 A1 | 10/2008 |
| GB | 1307351.5 | 10/2013 |
| WO | 2012/167208 A2 | 12/2012 |

* cited by examiner

*Primary Examiner* — Phillip A Johnston
*Assistant Examiner* — Hsien Tsai
(74) *Attorney, Agent, or Firm* — Benoit & Cote, Inc.

(57) ABSTRACT

The invention relates to the voltage supply of mass spectrometers, particularly electrostatic Kingdon ion analyzers, requiring extremely noise-free operating voltages. The invention proposes the use of passive charge storage devices, which operate without any feedback control and display no measurable noise or ripple if they are well shielded, instead of the usual actively operating high-voltage generators. Chemical charge storage devices or capacitors with good insulation can be used for this purpose. These may display slight voltage decreases due to continuous discharge, depending on their quality, but these decreases can be mathematically compensated.

18 Claims, 6 Drawing Sheets

VOLTAGE SUPPLIES FOR MASS SPECTROMETERS

BACKGROUND OF THE INVENTION

1. Field of the Invention

The invention relates to the supply of operating voltages for mass spectrometers, particularly Kingdon electrostatic ion traps and time-of-flight mass spectrometers.

2. Description of the Related Art

The term Kingdon ion traps refers to electrostatic ion traps in which ions can orbit around one or more inner longitudinal electrodes, or oscillate between inner longitudinal electrodes, and where an outer, enclosing housing is at a DC potential which the ions with a specified kinetic energy cannot reach. A very simple Kingdon ion trap consists of a rod (ideally an infinitely long rod) as the inner electrode and a surrounding tube as the housing or outer electrode. In special Kingdon ion traps which are suitable for use as mass spectrometers, the inner surfaces of the housing electrodes and the outer surfaces of the inner electrodes are designed so that, firstly, the motions of the ions in the longitudinal direction (z) of the Kingdon ion trap are decoupled from their motions in the transverse direction (x, y) or (r, $\phi$) and, secondly, a parabolic potential profile is generated in the longitudinal direction, in which the ions can oscillate harmonically. The frequencies of these oscillations can be determined from the measured image currents by means of Fourier transforms; they represent a measure for the mass of the ions.

In this publication, the terms "Kingdon ion traps" and "Kingdon mass analyzers" refer in particular to these special forms in which ions can oscillate harmonically in the longitudinal direction, decoupled from their motions in the transverse direction.

Figure 1:
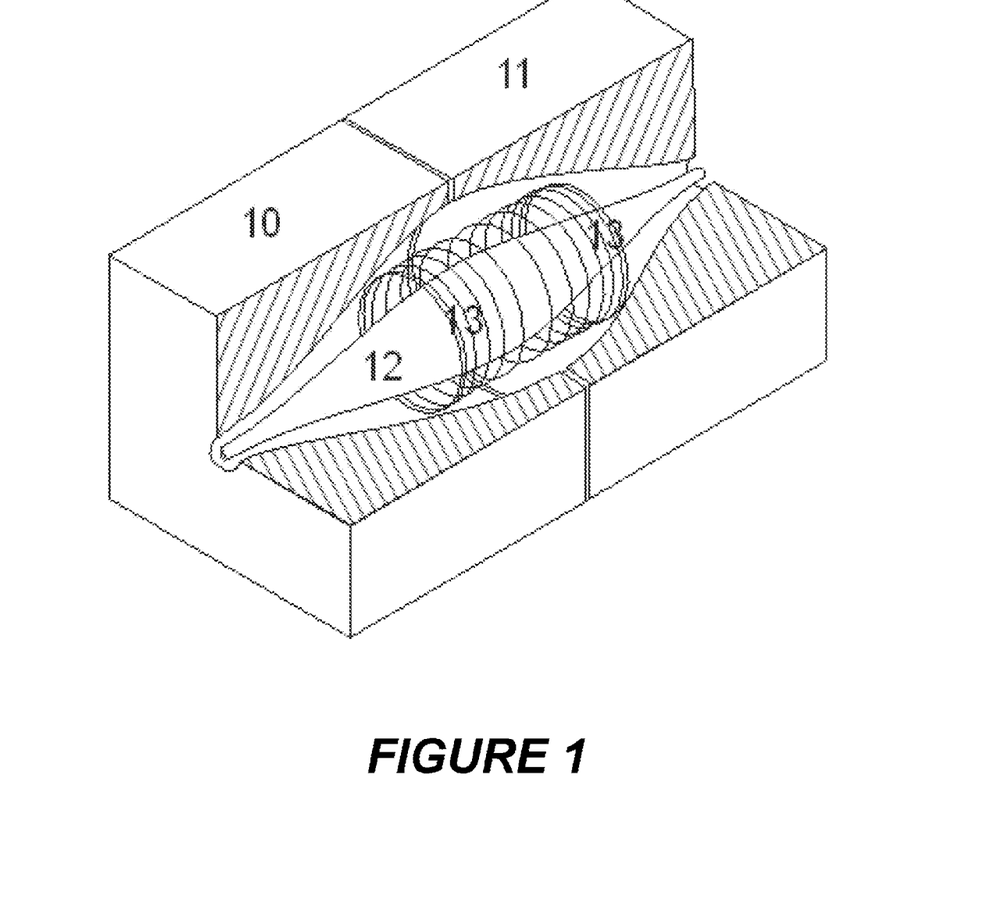
FIG. 1 shows an electrostatic Orbitrap ion trap according to A. A. Makarov in three-dimensional representation with the motion trajectories (13) of the ions around the inner electrode (12) in the centrally split housing (10, 11).

Different types of Kingdon ion trap with these characteristics are known. The patent specification U.S. Pat. No. 5,886,346 (A. A. Makarov) describes the fundamentals of a special Kingdon mass analyzer which was launched by Thermo-Fischer Scientific GmbH Bremen under the name Orbitrap®. The electrostatic ion trap here consists of a housing electrode which is split across the center and a single spindle-shaped coaxial inner electrode (FIG. 1). The housing electrode has an ion-repelling electric potential and the inner electrode an ion-attracting electric potential. The cross-sections of the inner surface of the housing electrodes and the outer surfaces of the inner electrodes are both circular. With the aid of a special ion-optical device and a special injection method, the ions are tangentially injected through an opening in the housing electrode and then orbit in the hyperlogarithmic electric potential of the ion trap. The kinetic injection energy of the ions is set so that the centripetal attractive forces and the centrifugal forces are in balance, and the ions therefore largely move on practically circular trajectories.

Figure 2:
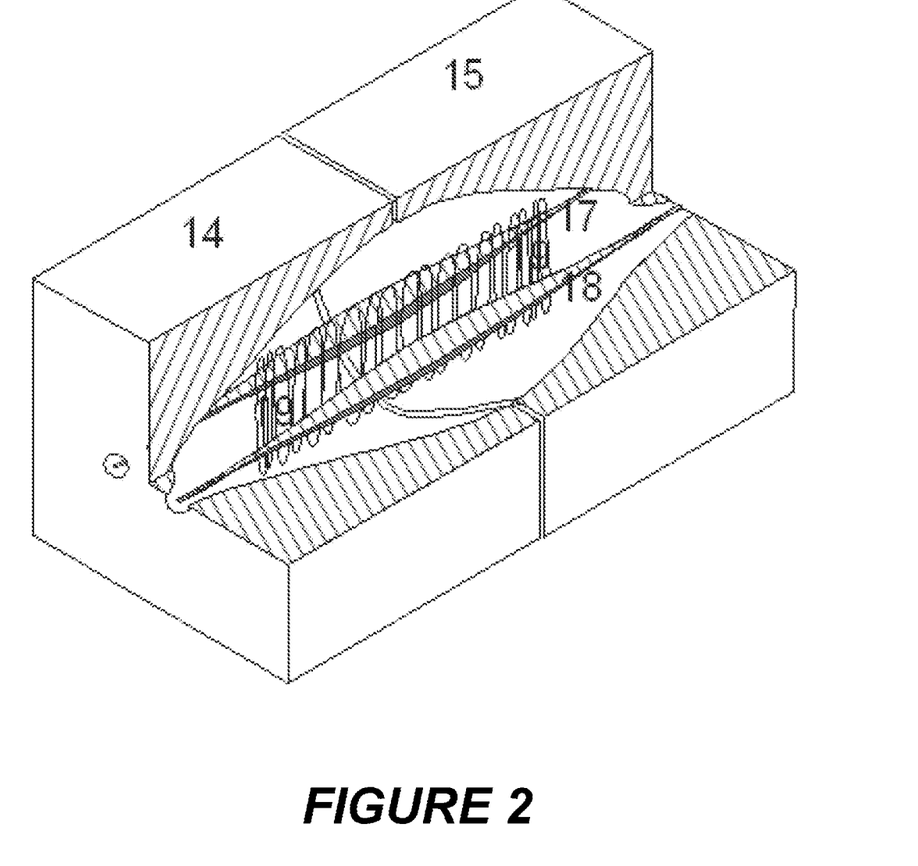
FIG. 2 shows an electrostatic second-order Cassini ion trap according to C. Köster in three-dimensional representation with a housing centrally split into two halves (14, 15) and two spindle-shaped inner electrodes (17, 18). In this illustration the ions execute oscillations (19) in the center plane between the two spindle-shaped inner electrodes.

In the document DE 10 2007 024 858 A1 (C. Köster), other types of Kingdon ion trap are described which, in one preferred embodiment, have precisely two inner electrodes (FIG. 2). Here too, the inner electrodes and the outer housing electrodes can be precisely shaped in such a way that a potential distribution is formed in which the longitudinal motions are decoupled from the transverse motions, and a parabolic potential well is created in the longitudinal direction to generate a harmonic oscillation. These "bipolar Cassini ion traps" or "second-order Cassini ion traps" are characterized by the fact that the ions not only can fly on complicated trajectories around the two inner electrodes, but can also oscillate transversely in the center plane between the two inner electrodes. The orbiting or transversely oscillating ions can then execute harmonic oscillations in the longitudinal direction.

All these Kingdon ion traps can be used as mass analyzers by measuring the image currents induced by the axial oscillations of the ions in bisected housing electrodes (or bisected inner electrodes), and by processing them appropriately with the aid of Fourier transforms to produce mass spectra. They therefore belong to the class of Fourier transform mass spectrometers (FT-MS). The electrodes can also be divided into more than two insulated partial segments in order to detect higher-order oscillations. The electric fields in the interior are generated by voltages between the inner and outer electrodes; the voltages are regularly between two to eight kilovolts, but can also be selected to be much higher. The higher the voltage, the higher will be the mass resolution and mass accuracy. This voltage is called "operating voltage" here; it determines the frequency with which the ions of a specific mass oscillate, and thus has a "frequency dispersive" effect and therefore a "mass-dispersive" effect, in contrast to lens voltages or voltages at beam deflectors for example.

In practical operation, the image currents are measured over a period of 0.1 to 10 seconds, depending on the analytical task; usually between 0.2 and 1 second in order to obtain several mass spectra of the substance peaks when the device is coupled to substance separators such as chromatographs. The longer the measured image current transient, the higher the mass resolving power.

As is known from ion cyclotron resonance mass spectrometers (ICR-MS), Fourier transform mass spectrometers provide extremely high mass resolutions and mass accuracies. This also applies to Kingdon mass spectrometers, but only if the ions can oscillate in the axial direction in an electric field with high temporal constancy. The electric field in Kingdon ion traps has an equivalent function to the magnetic field of the ICR mass spectrometers. The magnetic field of the ICR mass spectrometers is usually generated by superconducting solenoids, which have magnetic field strength decreases of only around $10^{-8}$ per day ($\approx 10^{-13}$ per second). Moreover, these magnetic fields have no superimposed noise or hum; even magnetic storms of the Earth's magnetic field are shielded.

Such temporal constancy and freedom from noise of the DC operating voltage for the electrostatic fields in Kingdon ion traps cannot be achieved with today's high-voltage generators. These high-voltage generators are usually based on the active switching of voltages and currents, which cause high voltages to be induced in the secondary winding of a transformer, and they have feedback control circuits (i.e. active regulation) which unavoidably generate small control oscillations. High-voltage generators comprising means for active switching of voltages and currents and/or feedback control circuits may be termed active high-voltage generators. Top-quality active high-voltage generators, specifically designed for these purposes, have a short-term constancy of around $10^{-6}$ per minute; often this is dependent on ambient temperature and supply voltage, albeit only slightly. Drifts of the operating voltage may occur toward both larger and smaller voltages, so they cannot be corrected prospectively. Even more serious, however, are voltage variations (ripple) due to control oscillations of the order of magnitude of $10^{-6}$ or more, sometimes also exhibiting superimpositions of different frequencies (residuals of the supply voltage frequency, for example). The voltage variations by ripples are on a short time scale, in particular on a time scale for acquiring a single mass spectrum or few subsequent mass spectra.

Figure 5:
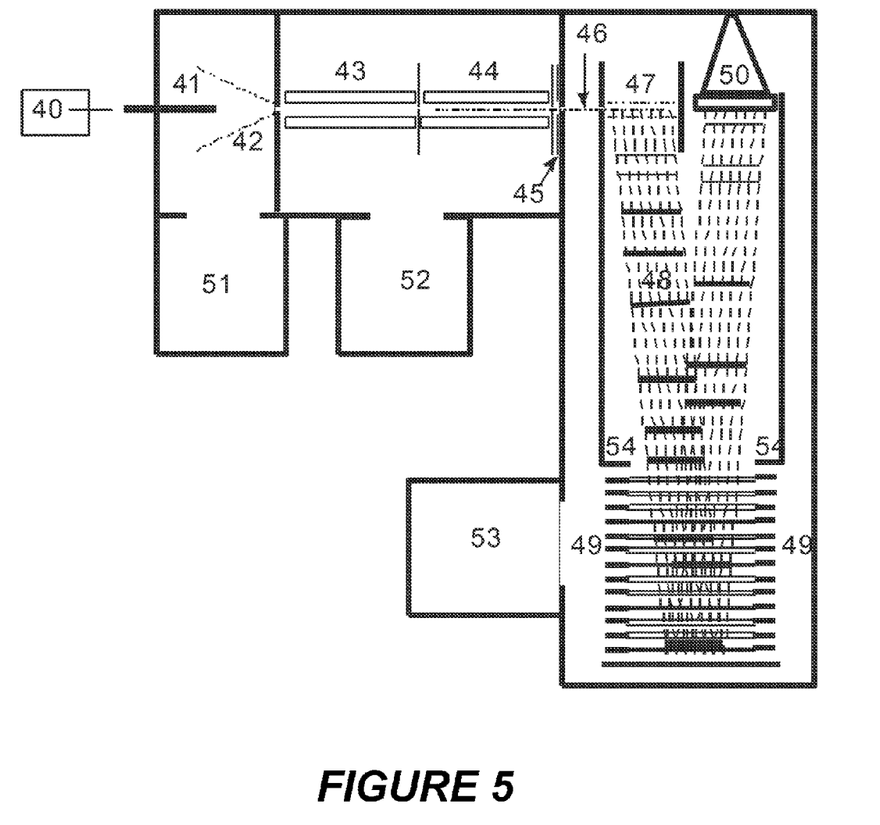

Noise-free DC operating voltages which are constant over time are required not only in Kingdon mass spectrometers, but also in other mass spectrometers. A time-of-flight mass spectrometer with orthogonal injection of the ions into an ion pulser, as is shown schematically in FIG. 5, is given here as a second example. The ion pulser usually pulses sections of a continuous ion beam, at right angles to the direction of flight of the ions, into an acceleration lens system, which accelerates the ions into the flight region of a time-of-flight mass spectrometer with a reflector. The acceleration is carried out with voltages of 10 to 20 kilovolts. This accelerating voltage determines the mass-dependent time of flight of the ions; it therefore has a "time-of-flight dispersive" effect The pulse rate of the ion pulser is usually 5 to 10 kilohertz, which means that 5000 to 10,000 time-of-flight spectra are acquired in one second, which are summed over a specified duration of 0.05 to 20 seconds, subjected to a peak recognition algorithm and then converted into a mass spectrum. The accelerating voltage is applied to an enclosure of the flight region, which is located within a grounded housing. The decelerating voltages on the individual diaphragms of the reflector must also be as free from drift, noise and ripple as possible when high mass resolutions and mass accuracies are required. Today, top-class time-of-flight mass spectrometers are designed to achieve mass accuracies which are far better than a millionth of the mass.

It should be noted here that slight, but constant, drifting of the DC operating voltages having a critical mass-dispersive effect, can be compensated by mathematical methods; but the noise cannot, and ripple only to a very limited extent. Voltage drifts can be corrected during the acquisition of an image current transient in a Kingdon mass analyzer: see the documents DE 10 2008 025 974 B3, GB 2 461 965 A or U.S. Pat. No. 7,964,842 B3 (C. Köster and K. Michelmann, 2008). Voltage drifts nevertheless have a negative effect because the analytical method then drifts away from its mass calibration, making it necessary to take special measures, such as the use of internal mass references. If the drifts always occur in the same direction and are very constant, however, then the resulting changes in the operating voltages can be automatically taken into account in mass calculations from the image current transients or the times of flight.

SUMMARY OF THE INVENTION

The invention proposes to use passive charge storage devices for the supply of high DC operating voltages for mass spectrometers, if the high DC operating voltage has a mass-dispersive effect (for short: mass-dispersive operating voltage), instead of using the active high-voltage generators used to date. The passive charge storage devices operate without a feedback control and, given suitable electric shielding, display no disturbing noise or voltage fluctuations (ripple). Although these charge storage devices display decreasing voltages over time due to continuous discharge via the insulation resistances, the decrease of voltage is temporally very constant compared to the duration of the spectrum acquisition, particularly if good temperature constancy is maintained. They can therefore be taken into account mathematically, as stated above, in the mass calculation from image current transients or times of flight. Charge storage devices may also show temporal drifts, for example due to temperature drifts.

In addition to the use of passive charge storage devices according to the invention for the supply of mass-dispersive operating voltages in mass spectrometers, the present invention also includes mass spectrometers which have at least one passive charge storage device and corresponding supply leads between the charge storage device and electrodes, to which mass-dispersive operating voltages are applied. The electrodes can be the inner and outer electrode of a Kingdon ion trap or the accelerating electrodes or reflector electrodes of a time-of-flight mass spectrometer, for example. The passive charge storage devices can consist of a multitude of electrochemical batteries (electrochemical charge storage devices) or one or more charged capacitors (capacitive charge storage devices), and preferably supply an operating voltage between two and thirty kilovolts, most preferably between three and twenty kilovolts.

A DC voltage of three kilovolts which has a drift of less than $10^{-10}$ per second during the main portion of its life time can thus be generated with 2000 electrochemical button cells each of 1.5 V, for example. The button cells can be accommodated in a volume of around one liter. The batteries and the supply leads are preferably electrically shielded, and if possible even magnetically, to protect against any external influences; in addition they can especially be kept at constant temperature. Surprisingly low cost voltage supplies with high voltages of up to around ten kilovolts and a life time of around five years can thus be produced, in particular at distinctly less costs than for a corresponding precisely regulated high-voltage generator. It is also possible to use rechargeable batteries (i.e. accumulators) here.

If the insulation of the electrodes to which the mass-dispersive operating voltages are applied in the mass spectrometers is very good, a purely capacitive charge storage device, which is best located in the vacuum system of the mass spectrometer itself, can also be used to supply the mass-dispersive operating voltage. A plate capacitor of about 500 picofarad, mounted rigidly in vacuum and not showing mechanical oscillations, may reduce the drift to less than $10^{-8}$ per second when connected, for example, to the electrodes of a Kingdon ion trap. The capacitor can easily be accommodated in a volume of only 200 milliliters. The voltage therefore decreases by a maximum of 40 ppm in one hour; this means the Kingdon trap can operate for many days without interruption.

If the mass-dispersive operating voltage, such as the accelerating voltage of a time-of-flight mass spectrometer, is supplied by a plate capacitor in the vacuum of the mass spectrometer, similarly low voltage decrease is measured. The voltages which are required at the individual diaphragms of the reflector can be generated with the aid of a capacitive voltage divider without any cross current (except the current across the insulators). The capacitor can occasionally be recharged again by a low-quality active high-voltage generator via a switch. The switch must be designed so that it does not transmit any influences when it is open. The mass calculation should be recalibrated after the recharging. The capacitor can be used for voltages of up to thirty kilovolts or more if it is appropriately designed.

The use of passive charge storage devices to supply mass-dispersive operating voltages in mass spectrometers according to the invention also has the advantage that the voltage supply can be made floating, i.e. it is independent of fluctuations in the line voltage or the grounding potential.

The invention furthermore comprises a method according to the invention for correcting the voltage drift of a passive charge storage device in measured mass spectra. The known or measured voltage decrease per unit time at the charge storage device can be automatically taken into account for calibrating the mass axis (calculation of mass values).

BRIEF DESCRIPTION OF THE DRAWINGS

FIG. 5 shows a greatly simplified schematic representation of a time-of-flight mass spectrometer with orthogonal ion injection in accordance with the Prior Art. In a normal operating mode, ions are generated at atmospheric pressure in an ion source (40) with a spray capillary and introduced into the vacuum system through an inlet capillary (41). An ion funnel (42) guides the ions into a first RF quadrupole rod system (43), which can be operated both as a simple ion guide, and also as a mass filter to select a species of parent ion to be fragmented. The unselected or selected ions are fed continuously into the storage device (44); selected ions can be fragmented by energetic collisions. Ions are extracted from the storage device (44) by the switchable extraction lens (45) at specified times; this lens shapes the ions into a fine primary beam (46) and sends them to the ion pulser (47). The ion pulser (47) pulses out a section of the primary ion beam (46) orthogonally in the direction of the drift region, whereby a strong post-acceleration lens system generates the new ion beam (48). The drift region is surrounded by a metal sheath (54) at high potential. The ion beam (48) is reflected in the decelerating potential of the reflector (49), whereby any velocity deviations are focused, and measured in the detector (50). The reflector is comprised of individual apertured diaphragms to which stepwise decreasing voltages have to be applied. The time-of-flight mass spectrometer is evacuated by the pumps (51), (52) and (53).

DETAILED DESCRIPTION

As stated above, the invention proposes the use of passive charge storage devices, instead of the usual active high-voltage generators, to supply the critical mass-dispersive operating voltage of mass spectrometers, such as Kingdon ion traps. These storage devices operate without any feedback control and are therefore free from control oscillations. Depending on the quality of the insulation, they may exhibit slight drifts due to continuous discharge across the insulation resistances. However, even relatively strong drifting can be compensated mathematically, as has also already been stated above, even if it occurs during the recording of the image current transient. But the drifts are usually so small that, for the acquisition of a mass spectrum, whether from an image current transient or from summed individual time-of-flight spectra, no drift compensations are necessary for the duration of the measurements for a mass spectrum. For longer periods amounting to days, during which hundreds or thousands of mass spectra are acquired, the drifts from scan to scan can be taken into account by simultaneous corrections applied to the calibration function, because the drifts of the operating voltage are well known and very constant. The drifts can also be corrected with the aid of internal reference substances.

Figure 3:
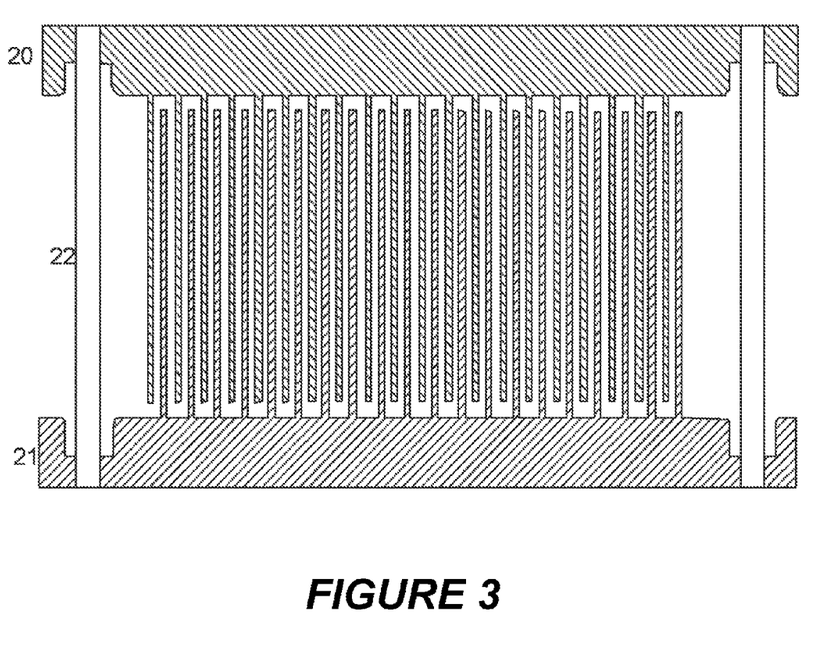
FIG. 3 depicts a vacuum plate capacitor with plate holders (20) and (21) and ceramic spacers (22). The ceramic spacers (22) are mounted in rounded blind holes in order to prevent an electric discharge along the ceramic surfaces, initiated by field emission of electrons. Twenty-five plates, each measuring five by five centimeters and with a spacing of one millimeter, produce a capacitance of around 500 picofarads.

A capacitor may be used as the charge storage device because, surprisingly, the insulation resistances in mass spectrometers, for example Kingdon ion traps, are extremely high, given an appropriate design. Kingdon ion traps of conventional size have electrical capacities of a few picofarads. If the voltage supply is removed during operation, a well-insulated Kingdon ion trap only displays a voltage decrease of less than $10^{-6}$ per second (1 ppm/s). It is already possible to work with this when only short image current transients of 0.1 to 1 second are to be measured and a mathematical drift correction is used, where necessary. This voltage decrease can, however, be significantly reduced by a capacitive storage device connected in parallel, if this does not introduce an interferingly low insulation resistance in addition. Best suited is a high-voltage vacuum plate capacitor, which is located in the vacuum system of the mass spectrometer itself. FIG. 3 shows a suitable plate capacitor which provides a capacitance of around 500 picofarads in a volume of around only 200 milliliters, and whose good insulation means it reduces the voltage decrease to less than $10^{-8}$ per second when connected to the electrodes of the Kingdon ion trap. This allows image current transients of up to 10 seconds duration to be processed without any drift compensations; or time-of-flight spectra can be summed over ten seconds without any corrections. Since the voltage decrease amounts to a maximum of 40 millionths in an hour, and only one percent after ten days, this means that many days of operation are possible after a single charging procedure, if the voltage decrease is taken into account by a simultaneous correction of the calibration function. Good insulation can be achieved by using ceramic or glass-ceramic materials, e.g. Macor®. After thorough baking in a vacuum, the conductivity of the insulators, which is essentially produced by surface resistances resulting from the adherence of moisture, decreases to almost zero. The resistance increases to more than $10^{15}$ ohms and then remains constant in the vacuum.

The capacitor must occasionally be recharged by a voltage generator. The voltage generator can be inexpensive because only a low quality is required. It is preferably located outside the vacuum system. Since the charging voltage is not accurately known due to the low quality of the voltage generator, it is expedient to carry out a measurement with calibration substances in order to calibrate the mass calculation function after each charging. The charging is carried out via a switch which is designed so that it and its supply leads can transfer as few interfering voltage influences as possible when the switch is open. It is preferable to use an electromechanical switch which is located outside the vacuum system, in the vicinity of the electrical voltage feedthrough, and well screened. The plate capacitor can be designed for voltages of up to thirty kilovolts or more.

Figure 6:
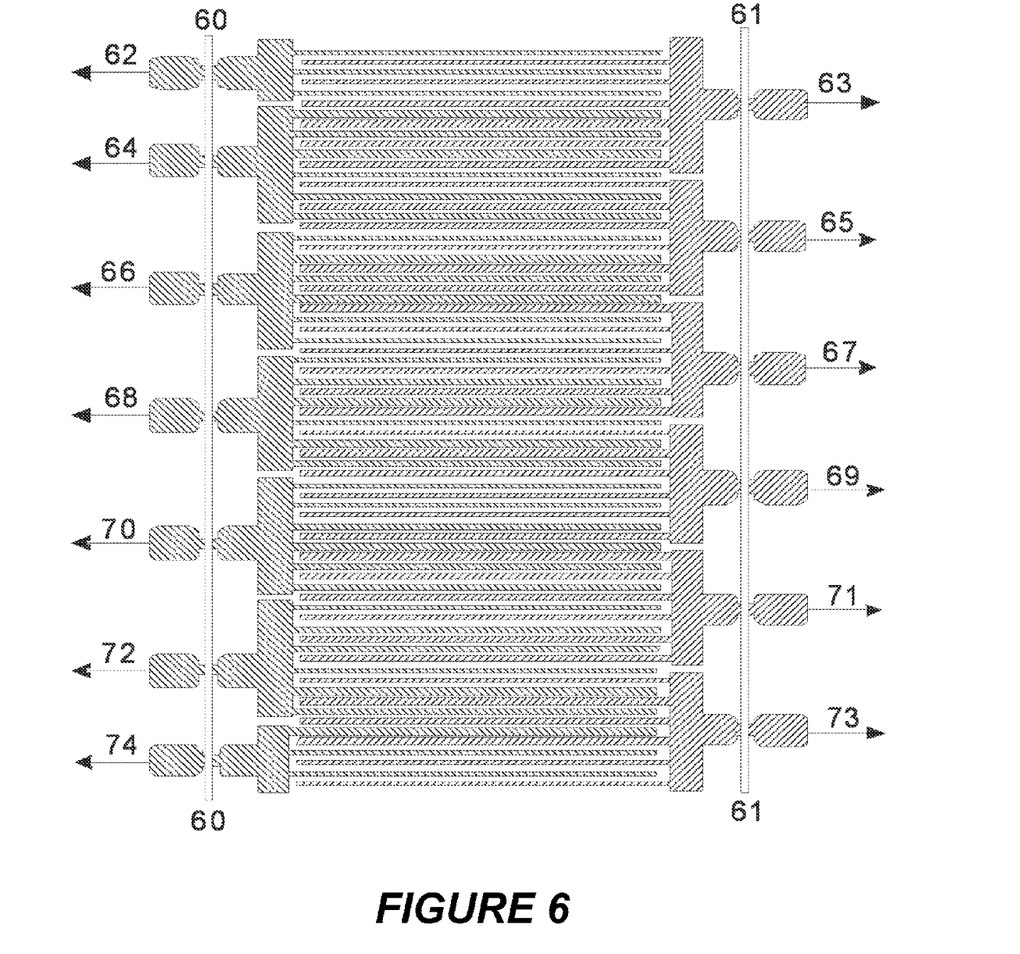
FIG. 6 shows the schematic of a capacitive voltage divider suitable for use in a vacuum. It has ceramic insulating rods (60) and (61), to which overlapping plate parts are fixed, which supply the partial voltages (62) to (74). These can be connected to the apertured diaphragms of the reflector (49) from FIG. 5.

In time-of-flight mass spectrometers, the operating voltage is applied to an inner flight tube (54), which surrounds the flight region with the ion beam (48). The reflector (49)

requires partial voltages, which are connected to the individual diaphragms of the reflector (49). These partial voltages can be generated by a capacitive voltage divider according to FIG. 6, which may be arranged in parallel to a main capacitor according to FIG. 3.

In many cases, chemical charge storage devices, i.e. electric batteries, can also be used as passive storage devices. It has already been mentioned above that a voltage of three kilovolts which has a drift of less than $10^{-10}$ per second during its operating life time can be generated with 2000 electrochemical batteries in the form of 1.5 V button cells. The button cells can be accommodated in a volume of around one liter.

Figure 4:
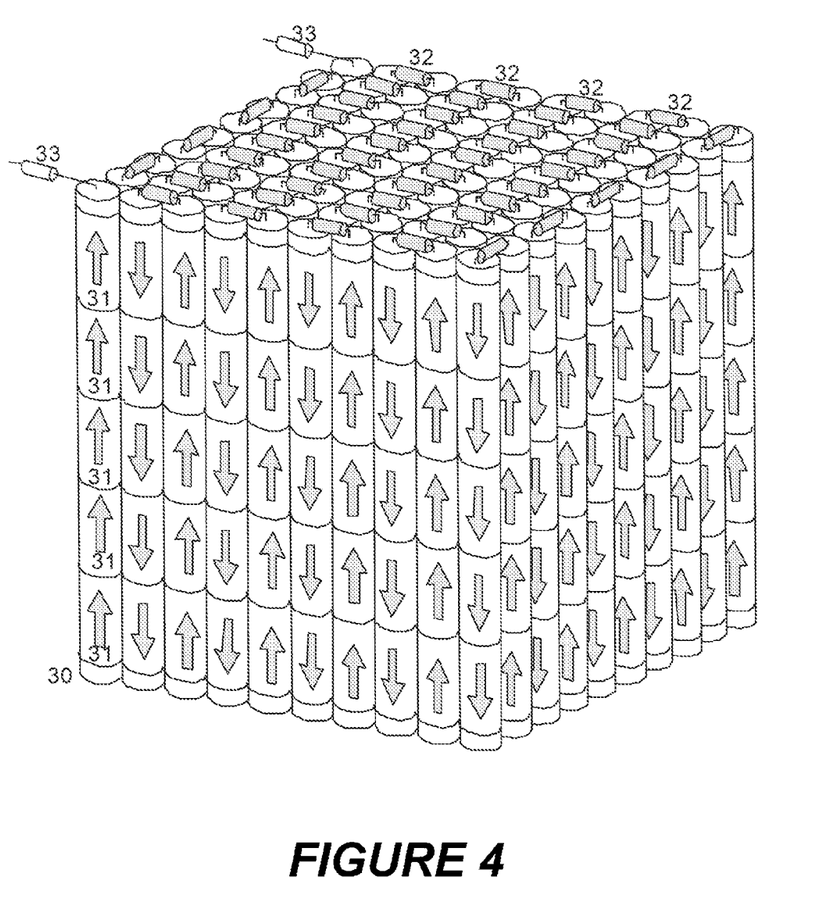
FIG. 4 depicts an assembly of 500 batteries (31), each of 12 volts, in plastic tubes (30), which supplies an operating voltage of 6 kilovolts. 100 resistors (32), each of 10 kΩ, increase the internal resistance to one megaohm and safeguard against short-circuits. Fuses (33) of 1 mA (slow-blow) protect against discharging in the event of external short-circuits. The compression springs which ensure secure contact between the batteries are not shown for reasons of clarity.

A great many types of battery can be used here. There are, for example, very low-cost 12 V alkali batteries (type designation LR23, measuring 10 mm in diameter and 28 mm in length) which are well suited. They can be stacked in series in flexible or rigid plastic tubes. If, as shown in FIG. 4, five of these batteries are each stacked in a plastic tube of 15 cm length and 12 millimeter diameter, and ten times ten of these stacks are assembled together, one obtains a battery with a voltage of six kilovolts in a volume of only 15×12×12 cm. This battery pack costs far less than a high-quality active high-voltage generator and has a life time of around five years.

The batteries and the supply leads must have very good electric shielding, and if possible even magnetic shielding, to protect against any external interferences. This can be achieved by metal boxes. In addition, the batteries must be stacked so as to be in good contact with each other. With short stacks, a good contact can be achieved with the aid of spring pressure; for longer stacks in flexible plastic tubes, the same effect can be achieved by pretensioned stretching of the tubes, in particular a flexible tube. Safety resistors and/or fuses should be inserted as protection against external short-circuits. The battery pack must be kept at constant temperature in its screening box. The techniques for temperature control are known to those skilled in the art; active voltage generators are also temperature-controlled. Preferably, the housing of the battery stack is flooded with an inert, dry gas, e.g. nitrogen.

The compact design of the battery pack in FIG. 4 can be modified in a variety of ways, of course. The pack, including the screening, can be shaped as a 19-inch rack, for example.

The decrease in the operating voltage over time is extremely constant with the batteries also; it can therefore be taken into account in the relevant mass calculation by means of simultaneous changes of the calibration function; the calibration can therefore remain valid for many days or even weeks. In order to increase the constancy of the drift, it is possible to use a discharging resistor of $10^{12}$ to $10^{14}$ ohms connected in parallel, which produces a constant discharge current but hardly shortens the life time at all.

Rechargeable batteries, which are available with approximately the same dimensions, can be used instead of ordinary batteries. They generally have a higher voltage decrease per unit of time, however, which can automatically be taken into account as a temporal change of the calibration function, similar to the procedure when ordinary batteries are used.

Filling the Kingdon ion traps with ions can require that the voltage between inner and outer electrodes is continuously increased by a small amount during the filling. Since the demands in terms of freedom from noise are not particularly high for the additional voltage, the increase can be brought about by an electronically controlled additional voltage from a voltage generator. This is connected in series with the voltage from the charge storage device with opposite polarity and is reduced to zero volts for measurement operations according to the requirements. It is best if this voltage supply is then separated completely from the voltage supplied by the charge storage device in order to avoid the transfer of any electrical influences.

The same applies to the voltage at the ion pulser (47) in the time-of-flight mass spectrometer. The ion pulser only ever switches a very small portion of the full accelerating voltage. This partial voltage is applied parallel to the operating voltage (accelerating voltage) and can be generated by an active voltage generator because here the electronic noise is again of minor importance. In any mass spectrometer the only voltages which must be kept noise-free and at constant drift are the high voltages which generate the mass dispersion: for Kingdon mass spectrometers, this is the operating voltage between inner and outer electrodes, which determines the oscillation frequency; for time-of-flight mass spectrometers it is the accelerating voltage, which determines the time of flight.

As examples for the use of passive charge storage devices according to the invention, only the Kingdon mass analyzers and the time-of-flight analyzers in time-of-flight mass spectrometers with orthogonal ion injection have been given here. But, of course, the invention can also be applied to all mass spectrometers for the operating voltages which are critical because they have a mass-dispersive effect, for example the accelerating voltages for ions in time-of-flight mass spectrometers with ionization by matrix-assisted laser desorption (MALDI-TOF MS), or in magnetic sector field instruments.

The invention claimed is:

1. A method for operating a mass spectrometer having a plurality of electrodes, the method comprising:
    generating a mass-dispersive operating voltage with a passive charge storage device using no active switching of voltages and no feedback control; and
    connecting the passive charge storage device to the electrodes so as to apply the mass-dispersive operating voltage to the electrodes during operation of the spectrometer.

2. The method according to claim 1, wherein the mass-dispersive operating voltage is a voltage between an inner electrode and outer electrode of an electrostatic Kingdon ion trap.

3. The method according to claim 1, wherein the mass-dispersive operating voltage is an accelerating voltage for injecting ions into the flight region of a time-of-flight analyzer.

4. The method according to claim 1, wherein the passive charge storage device is one of a capacitor and a battery and wherein each time the capacitor or battery is recharged, a calibration of the mass axis is carried out after charging.

5. The method according to claim 1, wherein a temporal decrease in the operating voltage supplied by the passive charge storage device is taken into account in a calibration function of the mass axis.

6. The method according to claim 1, wherein the mass-dispersive operating voltage is between two and thirty kilovolts.

7. A mass spectrometer comprising:
    a plurality of electrodes;
    a passive charge storage device that generates a mass-dispersive operating voltage using no active switching of voltages and no feedback control; and
    supply leads between the passive charge storage device and the electrodes such that the passive charge storage device provides the mass-dispersive operating voltage to the electrodes during operation of the spectrometer.

8. The mass spectrometer according to claim 7, wherein the passive charge storage device comprises one or more capacitors.

9. The mass spectrometer according to claim 8, wherein the capacitors are plate capacitors.

10. The mass spectrometer according to claim 9, wherein the plate capacitors are located in a vacuum.

11. The mass spectrometer according to claim 7, wherein the passive charge storage device comprises one or more electrochemical batteries.

12. The mass spectrometer according to claim 11, wherein the electrochemical batteries are rechargeable accumulators.

13. The mass spectrometer according to claim 7, wherein the passive charge storage device comprises internal resistors and/or fuses protecting against short-circuit discharging.

14. The mass spectrometer according to claim 7, wherein the mass spectrometer comprises an electrostatic Kingdon ion trap, and the electrodes are at least one inner electrode and one outer electrode.

15. The mass spectrometer according to claim 7, wherein the mass spectrometer comprises a time-of-flight mass spectrometer, and the electrodes are the accelerating electrodes of the time-of-flight mass spectrometer.

16. The mass spectrometer according to claim 7, wherein the mass spectrometer comprises a time-of-flight mass spectrometer with a reflector, and the electrodes are the reflector electrodes.

17. A method for operating an electrostatic Kingdon ion trap mass spectrometer comprising at least one inner electrode and an outer electrode, the method comprising:
providing a high resistance insulation between the at least one inner electrode and the outer electrode;
connecting a voltage supply to the electrodes for supplying a mass-dispersive operating voltage thereto;
removing the voltage supply from the electrodes such that the electrodes retain said mass-dispersive operating voltage; and
operating the mass spectrometer using said retained mass-dispersive operating voltage.

18. The method according to claim 17, wherein a temporal decrease in the operating voltage is taken into account in a calibration function of the mass axis.

* * * * *